(12) United States Patent
Ruijters et al.

(10) Patent No.: US 10,255,721 B2
(45) Date of Patent: Apr. 9, 2019

(54) MULTICAMERA DEVICE TRACKING (71) Applicant: KONINKLIJKE PHILIPS N.V., Eindhoven (NL)

(72) Inventors: Daniel Simon Anna Ruijters, Eindhoven (NL); Raoul Florent, Ville D'Avray (FR); Robert Johannes Frederik Homan, Batenburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/400,936

(22) PCT Filed: May 29, 2013

(86) PCT No.: PCT/IB2013/054424
§ 371 (c)(1),
(2) Date: Nov. 13, 2014

(87) PCT Pub. No.: WO2013/190409
PCT Pub. Date: Dec. 27, 2013

(65) Prior Publication Data
US 2015/0164607 A1    Jun. 18, 2015

(30) Foreign Application Priority Data
Jun. 20, 2012   (EP) .................................... 12305700

(51) Int. Cl.
*A61B 34/20* (2016.01)
*G06T 19/00* (2011.01)
(Continued)

(52) U.S. Cl.
CPC .............. *G06T 19/00* (2013.01); *A61B 34/20* (2016.02); *G06T 7/30* (2017.01); *G06T 19/20* (2013.01);
(Continued)

(58) Field of Classification Search
CPC .............. A61B 8/0841; A61B 19/5244; A61B 18/1492; A61B 34/20; A61B 2034/2055;
(Continued)

(56) References Cited

U.S. PATENT DOCUMENTS 5,740,802 A    4/1998 Nafis et al.
5,765,561 A    6/1998 Chen et al.
(Continued)

OTHER PUBLICATIONS

Kataoka et al., A Model for Relations Between Needle Deflection, Force, and Thickness on Needle Penetration, Oct. 2001 [retrieved Oct. 28, 2016], Medical Image Computing and Computer-Assisted Intervention: vol. 2208 of Lecture Notes in Computer Science, pp. 966-974. Retrieved from Internet: http://link.springer.com/chapter/10.1007/3-540-45468-3_115.*
(Continued)

*Primary Examiner* — Andrew M Moyer
*Assistant Examiner* — Dennis Rosario (57) ABSTRACT

The present invention relates to tracking an interventional device. In order to provide a facilitated and simplified real-time tracking of an interventional device, a medical imaging system (10) for tracking an interventional device is provided, that comprises an interface unit (12), and a processing unit (14). The interface unit is configured to provide first image data (18) of a first part of an interventional device, which first part is arranged outside an object. The first image data comprises 3D image data. The interface unit is configured to provide second image data (20) of a second part of the interventional device, which second part is a continuation of the first part, and which second part is arranged inside the object. The second image data comprises 2D image data. The processing unit is configured to compute a first 3D model portion of the interventional device based on the first image data, and to compute a second 3D model portion of the interventional device based on the second
(Continued)

image data and the first model portion. The interface unit is configured to provide data of a graphical representation (22) of the interventional device based on the first and second 3D model portions.

19 Claims, 10 Drawing Sheets (51) Int. Cl.
*G06T 19/20* (2011.01)
*G06T 7/30* (2017.01)
*A61B 34/10* (2016.01)
*A61B 90/00* (2016.01)

(52) U.S. Cl.
CPC . *A61B 2034/102* (2016.02); *A61B 2034/2057* (2016.02); *A61B 2090/371* (2016.02); *A61B 2090/376* (2016.02); *A61B 2090/378* (2016.02); *G06T 2207/10116* (2013.01); *G06T 2210/41* (2013.01)

(58) Field of Classification Search
CPC ....... A61B 34/30; A61B 34/25; A61B 90/361; A61B 34/10; A61B 2034/301; A61B 2034/102; A61B 2034/107; A61B 2090/378; A61B 17/3403; A61B 18/1477; A61B 8/4245; A61B 2018/1425; A61B 2034/2051; A61B 2017/003; A61B 17/00234; A61B 17/3478; G06F 19/3468; G06T 2207/30021; G06T 7/0012; G06T 2210/41; G06T 2207/10081; G06T 7/344; G06T 2207/10072; G06T 19/003; G06T 2207/30241; G06T 7/70; A61M 25/0147; G06K 2209/057; G09B 23/285
See application file for complete search history.

(56) References Cited

U.S. PATENT DOCUMENTS

| 5,930,329 | A  | * | 7/1999  | Navab ..................... A61B 90/36 378/98.12 |
| 6,122,541 | A  | * | 9/2000  | Cosman ................. A61B 90/10 600/426 |
| 6,490,471 | B2 |   | 12/2002 | Svenson |
| 6,626,832 | B1 | * | 9/2003  | Paltieli ................. A61B 8/0833 128/897 |
| 6,782,287 | B2 |   | 8/2004  | Grzeszczuk et al. |
| 7,641,638 | B2 | * | 1/2010  | Waxman et al. ............. 604/264 |
| 7,876,942 | B2 | * | 1/2011  | Gilboa ......................... 382/128 |
| 8,126,111 | B2 | * | 2/2012  | Uhde et al. ..................... 378/41 |
| 8,172,753 | B2 | * | 5/2012  | Halmann ...................... 600/443 |
| 8,553,839 | B2 |   | 10/2013 | Hendriks |
| 8,690,776 | B2 | * | 4/2014  | Razzaque ............ A61B 8/4245 600/407 |
| 9,251,721 | B2 | * | 2/2016  | Lampotang .......... G09B 23/285 |
| 9,572,539 | B2 | * | 2/2017  | Carrat ..................... A61B 5/061 |
| 2006/0258938 | A1 | * | 11/2006 | Hoffman ............ A61B 1/00193 600/424 |
| 2008/0020362 | A1 | * | 1/2008  | Cotin et al. ................... 434/267 |
| 2008/0137923 | A1 |   | 6/2008  | Spahn |
| 2010/0292565 | A1 |   | 11/2010 | Meyer et al. |
| 2011/0125011 | A1 |   | 5/2011  | Wieczorek et al. |
| 2011/0286653 | A1 |   | 11/2011 | Gorges |
| 2012/0156092 | A1 |   | 6/2012  | Suijver |
| 2012/0170824 | A1 |   | 7/2012  | Hendriks et al. |
| 2013/0211244 | A1 | * | 8/2013  | Nathaniel .............. A61B 5/055 600/424 |

OTHER PUBLICATIONS

Chan et al., A Needle Tracking Device for Ultrasound Guided Percutaneous Procedures, Nov. 2005 [retrieved Jul. 12, 2017], Ultrasound in Medicine & Biology, vol. 31, Issue 11, pp. 1469-1483. Retrieved from the Internet: http://www.sciencedirect.com/science/article/pii/S0301562905002899.*

State et al., Technologies for Augmented Reality Systems: Realizing Ultrasound-Guided Needle Biopsies, 1996 [retrieved Jul. 14, 2017], 1996 Proceedings of the 23rd Annual Conference on Computer Graphics and Interactive Tecniques, pp. 439-446. Retrieved from the Internet: http://dl.acm.org/citation.cfm?id=237283.*

Ayadi et al., Fully Automatic Needle Calibration for Robotic-Assisted Puncture on Small Animals, Nov. 8-9, 2007 [retrieved Nov. 17, 2017], 2007 IEEE/NIH Life Science Systems and Applications Workshop, pp. 85-88. Retrieved from the Internet: http://ieeexplore.ieee.org/xpls/icp.jsp?arnumber=4400890.*

Ding et al., Automatic needle segmentation in three-dimensional ultrasound images using two orthogonal two-dimensional image projections, Jan. 22, 2003 [retrieved Nov. 17, 2017], Medical Physics, vol. 30, Issue 2,pp. 222-234. Retrieved from the Internet: http://onlinelibrary.wiley.com/doi/10.1118/1.1538231/full.*

Schafer et al., Three-dimensional reconstruction of coronary stents in vivo based on motion compensated X-ray angiography, Mar. 22, 2007 [retrieved Aug. 2, 2018], Proc. SPIE: Medical Imaging 2007: Visualization and Image-Guided Procedures, vol. 6509, 8 total pages. Retrieved from the Internet: https://doi.org/10.1117/12.706439.*

Chan et al, "A Needle Tracking Device for Ultrasound Guided Percutaneous Procedures", Ultrasound in Medicine and Biology, vol. 31, No. 11, Nov. 2005, XP027605481, pp. 1469-1483.

Khosravi et al, "One-Step Needle Pose Estimation for Ultrasound Guided Biopsies", IEEE Engineering in Medicine and Biology Society, Aug. 2007, XP031336925, pp. 3343-3346.

Detsky, Jay S. et al "Reproducible Classification of Intarct Heterogeneity using Fuzzy Clustering on Multicontrast Delayed Enhancement Magnetic Resonance Images" IEEE Transactions on Medical Imaging, vol. 28, No. 10, Oct. 2009, pp. 1606-1613.

* cited by examiner

MULTICAMERA DEVICE TRACKING

CROSS-REFERENCE TO PRIOR APPLICATIONS

This application is the U.S. National Phase application under 35 U.S.C. § 371 of International Application Serial No. PCT/IB2013/054424, filed on May 29, 2013, which claims the benefit of European Patent Application 12305700.2 filed on Jun. 20, 2012. These applications are hereby incorporated by reference herein.

FIELD OF THE INVENTION

The present invention relates to a medical imaging system for tracking an interventional device, and a method for tracking an interventional device inserted partially inside an object, as well as to a computer program element and a computer readable medium.

BACKGROUND OF THE INVENTION

During examinations of an object, for example, interventional devices are used that can be inserted at least partially into an object, e.g. they extend inside the object. In case the inside of the object is invisible to a human eye, for example when examining a patient, the location, and thus also the range of the inserted interventional device cannot be followed without imaging systems that provide respective image data. For example, X-ray images are acquired to provide a better understanding of the present situation. An examination with an interventional device is, for example, a biopsy procedure. In US 2011/0125011 A1, it is described to acquire three-dimensional X-ray images as a roadmap. These are then combined with real-time 2D X-ray images that are angularly offset from each other. However, it has been shown that the acquisition of 3D images for a roadmap means additional preparation steps.

SUMMARY OF THE INVENTION

Thus, there may be a need to provide a facilitated and simplified real-time tracking of an interventional device.

The object of the present invention is solved by the subject-matter of the independent claims, wherein further embodiments are incorporated in the dependent claims.

It should be noted that the following described aspects of the invention apply also for the medical imaging system for tracking an interventional device, for the method for tracking an interventional device inserted partially inside an object, for the computer program element and for the computer readable medium.

According to a first aspect of the present invention, a medical imaging system for tracking an interventional device is provided, comprising an interface unit, and a processing unit. The interface unit is configured to provide first image data of a first part of an interventional device, which first part is arranged outside an object. The first image data comprises 3D image data. The interface unit is configured to provide second image data of a second part of the interventional device, which second part is a continuation of the first part, and which second part is arranged at least partially inside the object. The second image data comprises 2D image data. The processing unit is configured to compute a first 3D model portion of the interventional device based on the first image data, and to compute a second 3D model portion of the interventional device based on the second image data and the first model portion. The interface display unit is configured to provide data of a graphical representation of the interventional device based on the first and second 3D model portions.

The processing unit may be configured to register the first 3D image data and the second 2D image data.

According to an exemplary embodiment, a display unit is provided configured to display the graphical representation of the interventional device based on the first and second 3D model portions.

According to an exemplary embodiment, the medical imaging system further comprises a first image acquisition device, and a second image acquisition device. The first image acquisition device is configured to acquire the first image data. The second image acquisition device is configured to acquire the second image data.

The first portion is also referred to as an outside portion and the second portion is referred to as an inserted portion. The interventional device may be an elongated device with a longitudinal axis, which is aligned with an insertion direction.

According to an exemplary embodiment, the first image data is provided by at least two optical cameras. The second image data may be provided by an X-ray imaging arrangement. Alternatively, or in addition an ultrasound imaging arrangement may be provided.

For example, the first image acquisition device is an optical imaging system providing optical, i.e. visible images. The second image acquisition device is an X-ray imaging system providing X-ray image data or an ultrasound imaging device providing ultrasound image data.

The first and second image data may be are acquired live, i.e. in real-time. The first image acquisition device may comprise an optical image acquisition device with at least two cameras. The first image data may be provided by laser scanners, depth cameras, e.g. time-of-flight cameras, structured light cameras, ultrasound through air and the like. Another possibility is radar. The second image acquisition device comprises an X-ray image acquisition device or an ultrasound image acquisition device, according to an example. The X-ray image acquisition device may be an X-ray image acquisition device with an X-ray source and an X-ray detector.

According to an exemplary embodiment, the processing unit is configured to register the first 3D image data and the second 2D image data. The display is configured to display the first 3D image data and the second 2D image data in a combined image together with a model representation of the interventional device based on the first and second model portions.

According to an exemplary embodiment, the processing unit is configured to combine the first model portion and the second model portion to form a 3D model of the interventional device.

According to an exemplary embodiment, the processing unit is configured to determine a bounding space, in which the interventional device is located'. The processing unit is further configured to determine the bounding space based on the first model portion and the second model portion, and/or on the model of the interventional device.

According to an exemplary embodiment, the processing unit is configured to determine a bounding box, in which a predetermined part of the interventional device is located.

According to an exemplary embodiment, the interventional device is a flexible interventional device configured for a bending in simple curve geometries. The processing unit is configured to determine two possible bending poses of the needle. And the display is configured to present the bending poses to the user.

According to an exemplary embodiment, the processing unit is configured to determine a bending of the interventional device for the first image data. The processing unit is configured to predict a bending of the interventional device inside the object based on the determined bending in the first image data.

According to an exemplary embodiment, the processing unit is configured to register the first 3D image data and the second 2D image data. The display unit is configured to display the registered images in a combined image.

According to a second aspect of the present invention, a method for tracking an interventional device inserted partially inside an object is provided, comprising the steps:
a) acquiring first image data of a first part of an interventional device, which first part is arranged outside an object, wherein the first image data comprises 3D image data;
b) acquiring second image data of a second part of the interventional device, which second part is a continuation of the first part, and which second part is arranged inside the object, wherein the second image data comprises 2D image data;
c) computing a first 3D model portion of the interventional device based on the first image data; and
d) computing a second 3D model portion of the interventional device based on the second image data and the first model portion.

According to an exemplary embodiment, a step e) is provided, in which the first model portion and the second model portion are combined to form a 3D model of the interventional device.

According to an exemplary embodiment, a step f) is provided, in which a bounding space is determined, in which the interventional device is located. The determination of the bounding space is based on the first model portion and the second model portion, and/or on the model of the interventional device.

The term "bounding space" refers to the space that defines the possible boundaries of the area in which the device may be positioned, i.e. the determined location considering certain deviations that are possible and reasonable.

According to an exemplary embodiment, a bounding box is determined, in which a predetermined part of the interventional device is located.

In one example, a confidence volume is determined for the range of location of the part of the device arranged inside the object. Based on the length of the device, for example a needle, it is possible to determine the length of the portion arranged outside the body on behalf of the 3D image data. Further, the length of the portion inside the object can be determined. Together with the direction, i.e. orientation of the outside part, the insertion point is the starting point for the confidence volume. Depending on the rigidity, i.e. flexibility of the device, the inside part could be bended inside the object, i.e. deviate from the straight or linear direction as given by the orientation. The possible space in which the device could thus be located can be visualized to the user as the confidence volume.

For example, the interventional device is rigid, wherein a location of the predetermined part is determined. In a further example, the interventional device is flexible, wherein a location of the predetermined part is determined.

In one example, the bounding spatial region, i.e. the bounding space, is presented to the user in relation with image data of the object.

In another example, a planned needle path is shown overlay to the determined model.

In a further example, in case of a flexible interventional device configured for a bending in simple curve geometries, two possible bending poses of the needle are determined and presented to the user.

According to an aspect of the present invention, an interventional device tracking, e.g. needle tracking, is provided that delivers 3D information inside, for example, the patient's body, using, for example, a multi-optical camera setup. For example, the interventional device profile in three dimensions, corresponding to the outside of the object, which is obtained from, for example, a video setup, is combined with the two-dimensional device footprint corresponding to the object's inside, which 2D needle or device footprint is obtained from needle tracking, for example, in live X-ray images. In a further option, an a-priori known length of the device, i.e. a length known before using the device, can be used in these combination steps. Thus, the present approach allows the modelling of the full needle device extent, i.e. the outside and inside parts, and the determining where the object's front end is located. This determination may be achieved with various degrees of accuracy, depending on assumptions and needle types. For example, rigid needles can be located with high perfection. The provision of three-dimensional image data of the outside portion of the device can be arranged, for example, with optical cameras, thus providing an enhanced and facilitated way of providing the 3D outside data. Further, the provision of image data of the inside of the object is having a reduced effort, since only two-dimensional image data is provided. However, the 3D outside data is used for providing the missing third dimension of the device inside, i.e. 3D image data inside the object is provided by the combination of the 3D outside data and the 2D inside data. For example, the interventional device is a needle. The needle path in the X-ray image does not reveal the needle pose perpendicular to the X-ray image plane. However, in order to assure that the planned target is hit and that critical anatomical structures are avoided, this information is needed in particular. The present invention allows determining the needle pose perpendicular to the X-ray image, or at least a limited region in which the needle can be found, without the necessity to move the X-ray gantry or other additional measurements. By tracking the needle in the optical camera images, and combining the information from multiple cameras, it is possible to accurately determine the actual 3D path of the needle for part that is outside the patient's body. Further, the needle is tracked in the 2D live X-ray image and the full needle extent (outside plus inside) is modelled, based on the combination of the 3D video needle profile (outside part) and on the 2D X-ray needle footprint (inside part). Further, as an option, it is possible to introduce the a-priori known needle's length in this modelling.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
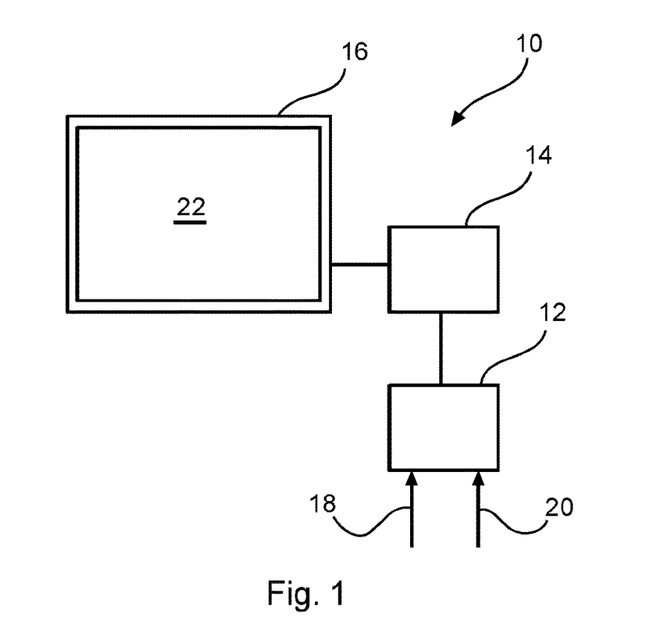
FIG. 1 shows an exemplary embodiment of a medical imaging system in a first basic setup.

FIG. 1 shows a medical imaging system 10 for tracking an interventional device in a first example, comprising an interface unit 12 and a processing unit 14. As an option, a display unit 16 may be provided. The interface 12 unit is configured to provide first image data, indicated with a first arrow 18, of a first part of an interventional device, which first part is arranged outside an object. The first image data comprises 3D image data. The interface unit 12 is further configured to provide second image data, indicated with a second arrow 20, of a second part of the interventional device, which second part is a continuation of the first part, and which second part is arranged at least partially inside the object. The second image data comprises 2D image data. The processing unit 14 is configured to compute a first 3D model portion of the interventional device based on the first image data, and to compute a second 3D model portion of the interventional device based on the second image data of the first model portion. The interface unit is configured to provide data of a graphical representation 22 of the interventional device based on the first and second 3D model portions.

The display unit 16 is configured to display the graphical representation 22 (not further shown in detail in FIG. 1) of the interventional device.

Figure 2:
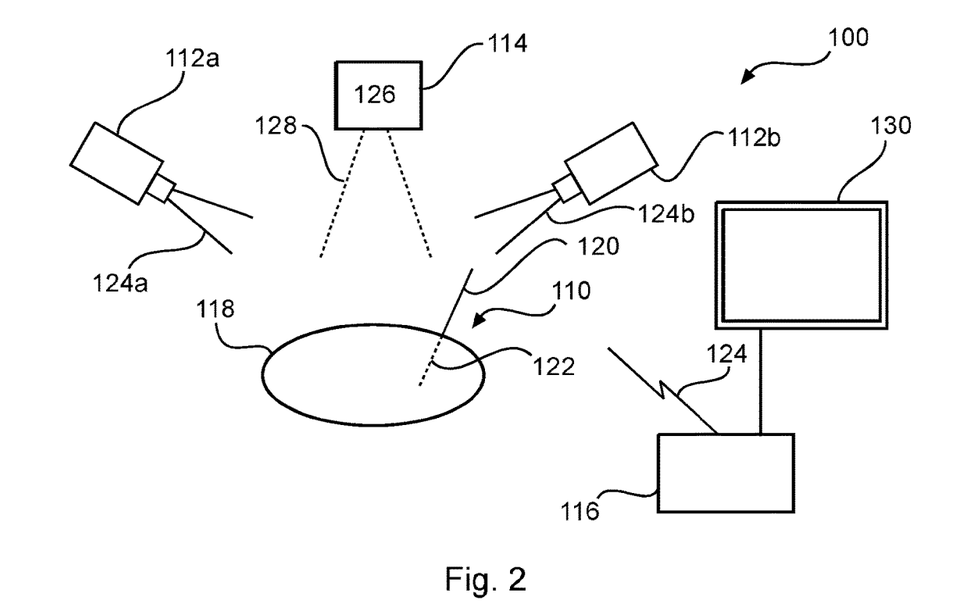
FIG. 2 shows a medical imaging system according to an exemplary embodiment in a further schematic setup.

FIG. 2 shows a further example of a medical imaging system 100 for tracking an interventional device 110, wherein the medical imaging system 100 comprises a first image acquisition device 112, for example shown as a first camera 112a and a second camera 112b. Further, a second image acquisition device 114 is provided, together with a processing unit 116. The first image acquisition device 112 is configured to acquire the first image data comprising 3D image information, or 3D image data, of a first part of an interventional device, which first part is arranged outside an object, for example a patient 118. The first part of the interventional device 110 is indicated with reference numeral 120. The second image acquisition device 114 is configured to acquire the second image data comprising 2D image information, or 2D image data, of a second part of the interventional device, which second part is a continuation of the first part, and which second part is arranged, e.g. inserted, at least partially inside the object. The second part is indicated with reference numeral 122. The processing unit 116, being in data communication or data connection 124 with the other components, is configured to compute a first 3D model portion of the interventional device based on the first image data, and to compute a second 3D model portion of the interventional device based on the second image data and the first model portion. It should be noted that the interface unit as mentioned above is not further shown.

For example, the first image data is provided by at least two optical cameras 112a and 112b. The respective image acquisition is indicated with a camera viewing beam 124a and 124b, respectively. Instead of the two cameras, a stereo camera may be provided, for example with distance determination means.

The second image data may be provided by an X-ray imaging arrangement 126, not further shown. A dotted beam structure 128 indicates a respective X-ray beam. It must be noted that further details, for example a detector, are not further shown in FIG. 2.

According to a further example (not further shown), the second image data is provided by an ultrasound imaging arrangement.

The processing unit 116 is configured to register the first 3D image data and the second 2D image data. Further, a display 130 is provided, which is configured to display the first 3D image data and the second 2D image data in a combined image together with a model representation of the interventional device based on the first and second model portions. However, it must be noted, that the display 130, although shown in relation with the other features of FIG. 2, does not represent a feature that is absolutely necessary for the embodiment of the other features. Thus, the display 130, shown in FIG. 2, must be seen as an option.

Figure 3:
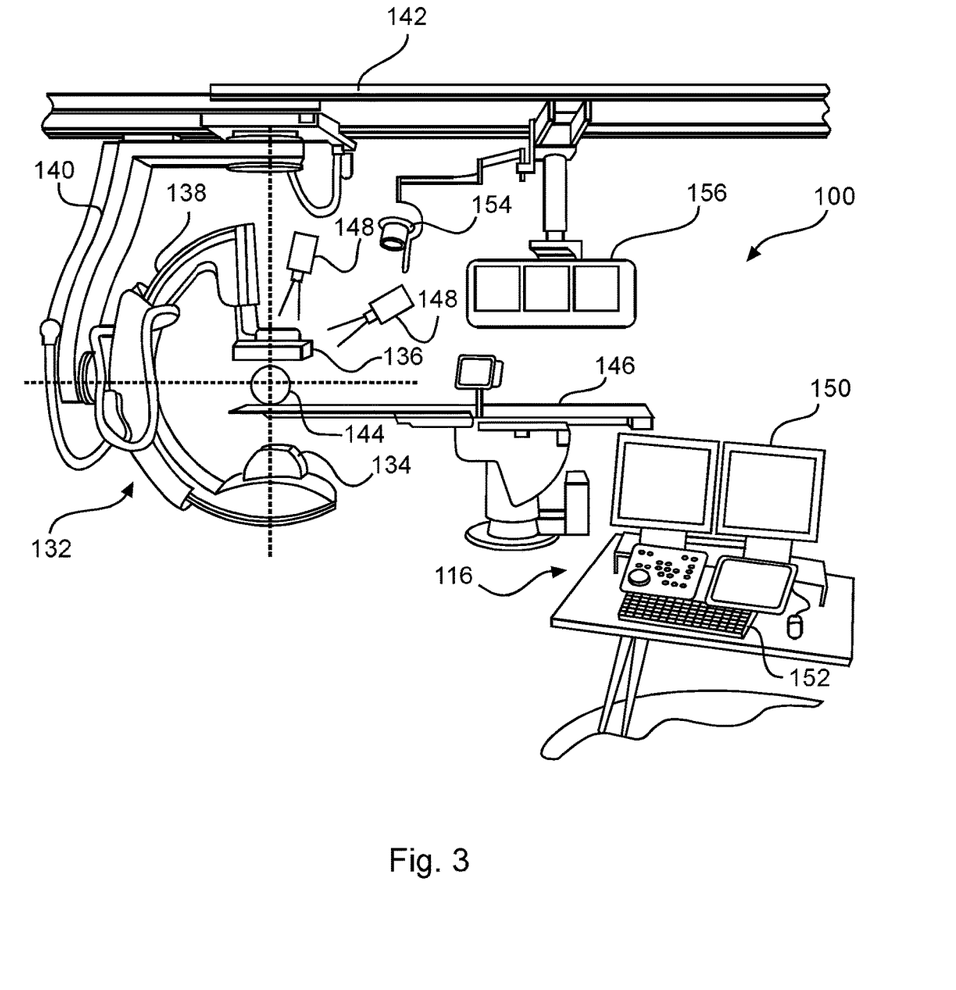
FIG. 3 shows a further example of medical imaging system with an X-ray image acquisition unit as a second image acquisition device.

FIG. 3 shows a further example of a medical imaging system 100, comprising a C-arm X-ray imaging arrangement 132, with an X-ray source 134 and an X-ray detector 136 provided on opposite ends of a C-arm structure 138. Further, a movable support 140 is shown, together with a ceiling mounting system 142. For example, an object 144 is shown supported on a movable or adaptable support, for example a patient table 146. Further, two cameras 148 are shown for the first image acquisition device. Still further, the processing unit 116 is shown in the foreground with monitors 150 and user interfaces 152, for example a mouse, a keyboard, a touchpad or other control panels. Further, lighting equipment 154 is shown, together with a larger display arrangement 156. Instead of a C-arm, also other types of X-ray image acquisition can be provided.

Figure 4:
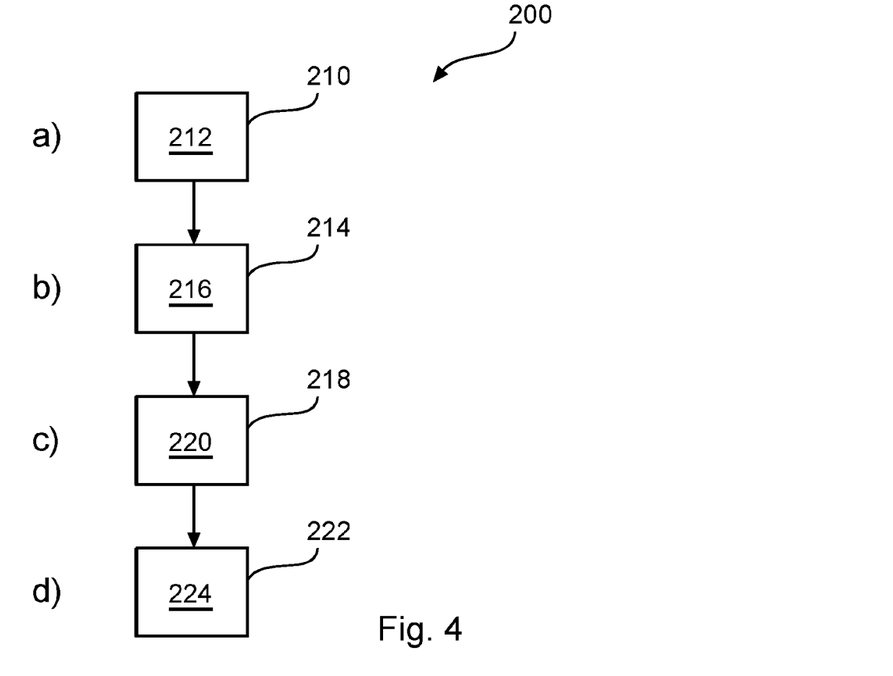
FIG. 4 shows basic steps of an exemplary embodiment of a method for tracking an interventional device.

FIG. 4 shows a method 200 for tracking an interventional device inserted partially inside an object, comprising the following steps. In a first step 210, first image data 212 of a first part of an interventional device is acquired, which first part is arranged outside an object, wherein the first image data comprises 3D image data. In a second step 214, second image data 216 is acquired of a second part of the interventional device, which second part is a continuation of the first part, and which second part is arranged inside the object, wherein the second image data comprises 2D image data. In a third step 218, a first 3D model portion 220 of the interventional device is computed based on the first image data. In a fourth step 222, a second 3D model portion 224 of the interventional device is computed based on the second image data and the first model portion.

The first step 210 is also referred to as step a), the second step 214 as step b), the third step 218 as step c), and the fourth step 222 as step d).

The interventional device position perpendicular to the image plane of the second image data may be determined based on the 3D information provided by the first image data. For the position, a limited region, in which the device can be found, may be determined. The first part is also referred to as first fragment and the second part is also referred to as second fragment.

For computing the first model portion, the interventional device is determined in the first image data, and for computing the second model portion, the interventional device is determined in the second image data.

For computing the first model portion, the interventional device may be tracked in the first image data, and for computing the second model portion, the interventional device is tracked in the second image data.

For tracking the interventional device, a first end of the interventional device may be tracked and an entry point, where the interventional device enters the object's surface, is determined.

Figure 5:
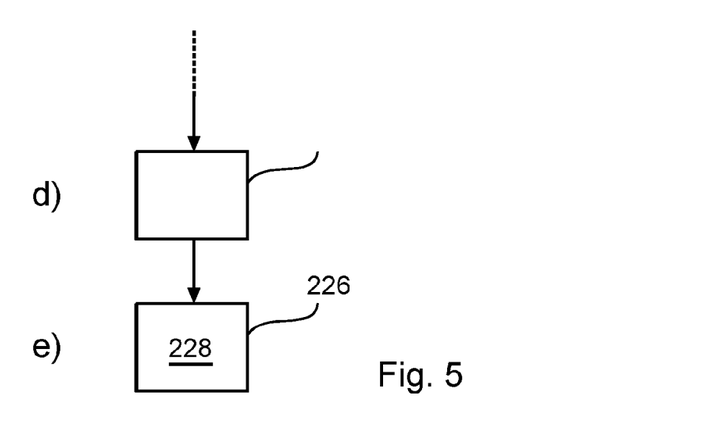
FIGS. 5 and 6 show further examples of further method steps.

FIG. 5 shows a further example of the method, wherein a fifth step 226 is provided, which is also referred to as step e). In step e), the first model portion and the second model portion are combined to form a 3D model 228 of the interventional device.

For example, for computing of the second model portion in step e), this is also based on a predetermined length of the interventional device. As mentioned above, the interventional device may be a biopsy needle. The fifth step 226 is also referred to as step e).

Figure 6:
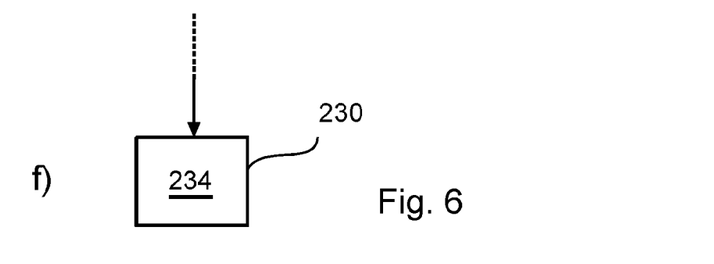

As shown in FIG. 6, a sixth step 230 may be provided, in which a determination 234 of a bounding space takes place, in which bounding space the interventional device is located. The determination of the bounding space is based on the first model portion and the second model portion; and/or on the model of the interventional device. The bounding space may also be referred to as bounding spatial region. The sixth step 230 is also referred to as step f).

It must be noted that step f) can be provided in combination with step e), following step e), or in combination with steps a) to d), following step d).

For example, a bounding box may be determined, in which a predetermined part of the interventional device is located.

The bounding spatial region may be presented to the user in relation with image data of the object.

According to a further example (not further shown), a device track for the interventional device is computed based on at least the first model portion. For example, the interventional device may be a biopsy needle and the device track is a needle path.

In case of a flexible interventional device configured for a bending in simple curve geometries, two possible bending poses of the needle are determined and presented to the user.

For example, a bending of the interventional device is determined for the first image data; and a bending of the interventional device inside the object is predicted, based on the determined bending in the first image data.

For example, a volumetric region is determined indicating the expected position of the interventional device. A bending of the interventional device is determined for the first part of the interventional device; and a bending of the interventional device is determined for the second part of the interventional device. For example, a cone-shaped region is determined in which the second part is located.

According to a further example (not further shown), the first 3D image data and the second 2D image data are registered and displayed in a combined image.

Figure 7:
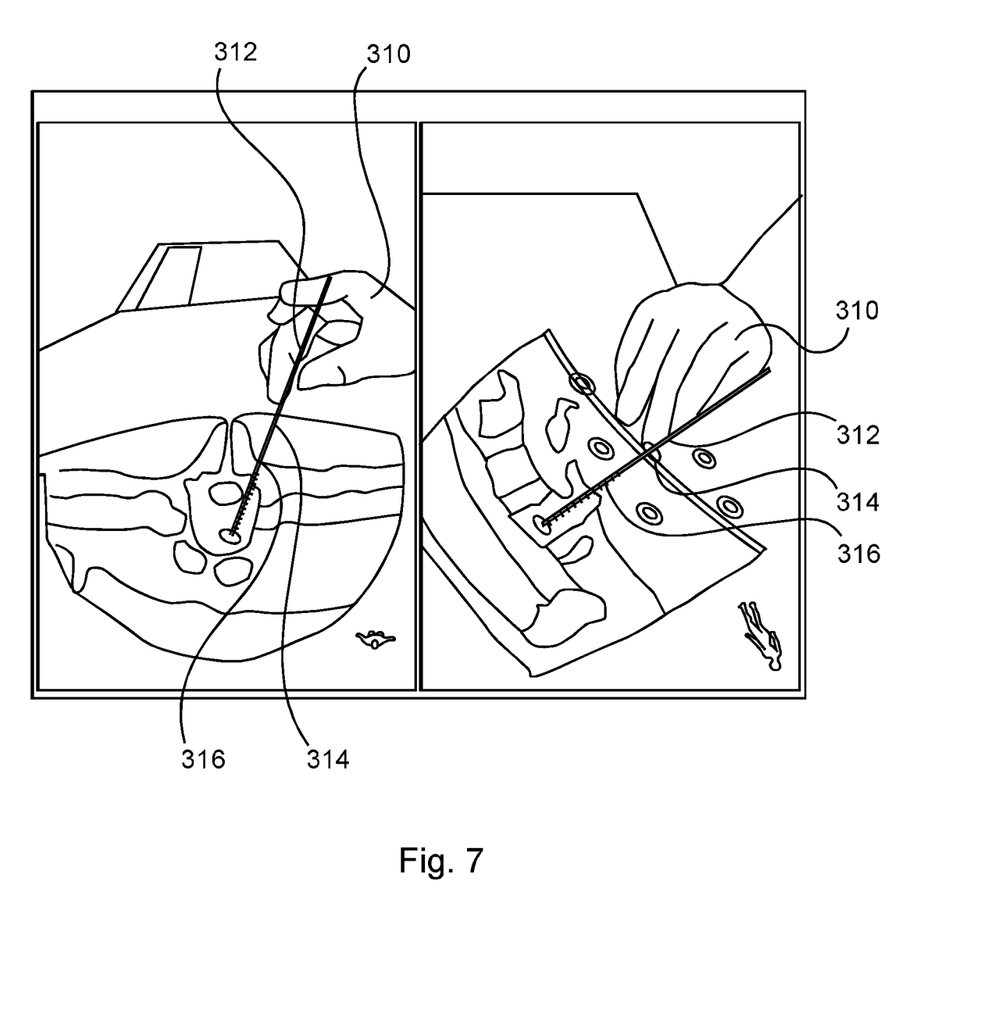
FIGS. 7 and 8 show different examples of graphical representations according to exemplary embodiments.

FIG. 7 shows an example of a displayed image, in which optical images from two cameras are fused with a planned needle path and a three-dimensional X-ray reconstruction. In the left image, a user's hand 310 is visible, holding a needle 312. A small circle 314 indicates an insertion point of the needle, i.e. a point where the needle enters the inside of the patient. Further, the part of the needle inside the object, i.e. the patient for example, is also indicated with reference numeral 316. Similar is also shown in right half of FIG. 7.

Figure 8:
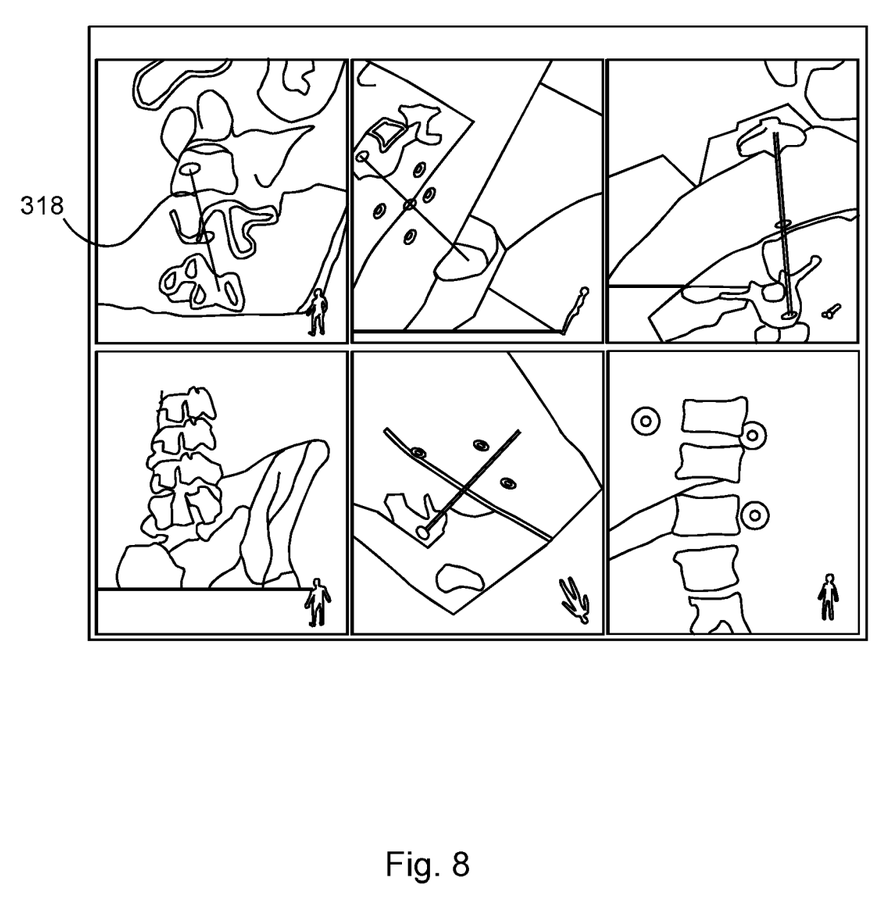

In FIG. 8, a planned needle path 318 is shown in the upper left half. Further, a live fluoroscopy image with fused overlay is shown in the upper row in the middle portion and the right portion, as well as in the lower row for the left portion and the middle portion.

According to a further example, the above described approach allows achieving the following features: the bounding region, in which the needle, and in particular the needle tip, can possibly be present, can be determined, and visualized to a physician. Using this information, it can be determined that vital anatomical parts have not been hit, which saves X-ray dose and time, since in that case no further verification is needed. Using this information, the physician can decide to move the gantry to another angle to verify the needle location, in case the bounding region seems to be critical. Using this information, the physician can decide to make a 3D reconstruction, for example using Philips XperCT, to verify the needle location. Using the assumption that the needle bends only making a simple curve, only one concavity possible, the two possible poses can be indicated to the physician, which shall also be described in the following. Using the bending outside the body, detected by the optical cameras for example, the bending inside the body can be predicted. If a needle is rigid, the exact needle tip location can be determined in three-dimension, i.e. the bounding box is shrunk to a point.

Figure 9A:
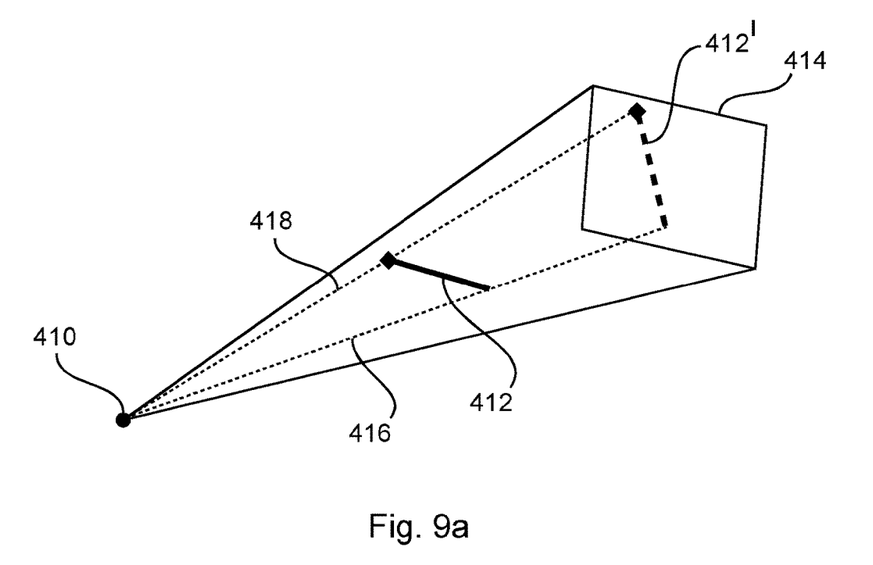
FIGS. 9a to 9e show further examples of different aspects in relation with the present invention.
Figure 10:
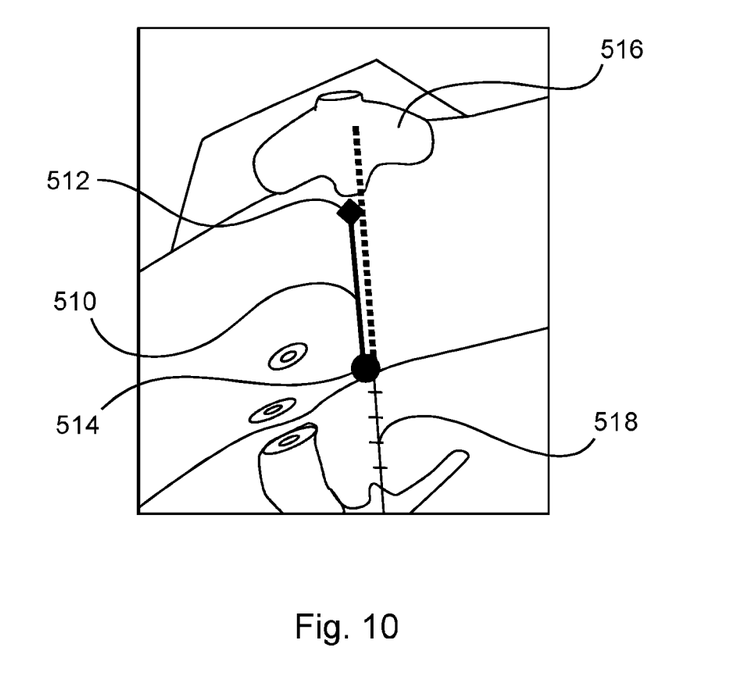
FIG. 10 shows a further example of a graphical representation according to an exemplary embodiment.

With respect to FIG. 9 et seq., some aspects shall be further explained. In FIG. 9a, an X-ray source 410 is shown, and a needle 412 arranged between the X-ray source 410 and an X-ray detector 414. On the detector 414, a projection 412' of the needle is indicated with a dotted line. When only the X-ray image and, for example, a C-arm gantry pose are given, it is impossible to know the exact location of the needle. The amount of possible needle positions within the dashed triangle, indicated with dashed lines 416, 418, is infinite. In order to overcome this, it is necessary to track the needle in the optical images, for example shown in FIG. 10, showing a first line 510 indicating the needle, where a diamond shape indicates a head 512, and a ball shape 514 indicates a skin entry point. Further, the optical images show a handle portion 516. A further line 518 indicates a possible position inside the object.

Figure 9B:
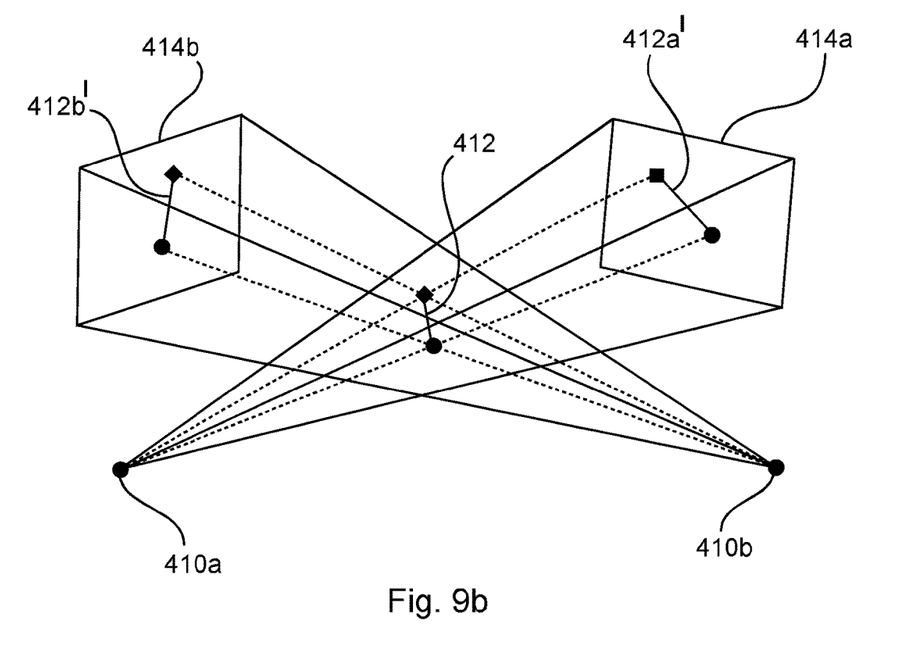

FIG. 9b shows the needle 412 viewed under two different viewing angles, namely from a first focal spot 410a and a second focal spot 410b. The first focal spot is projecting towards a first detector 414a, and the second focal spot 410b is projecting towards a detector 414b. Thus, respective needle projections 412'a and 412'b are provided. The tracked needle fragment from the optical images can be reprojected into 3D space. The intersection of the reprojections delivers the actual needle fragment location in 3D space. It must be noted that FIG. 9b relates to the image data provided by the optical cameras, for example. The lines and projections indicating the needle 412 are also shown with a diamond shape on one end, representing the needle's head, and a ball shape at the other end, indicating the needle's entry portion.

Figure 9C:
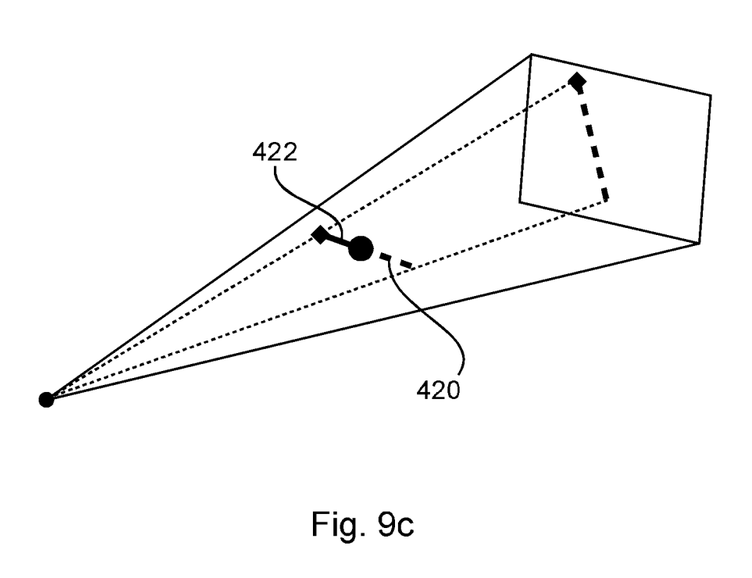

FIG. 9c refers to a first embodiment for stiff or straight needles, where the combination of the 3D position of the needle fragment outside the patient's body, as taken from the optical camera images (see FIG. 9b), and the X-ray image, as described in FIG. 9a, is combined to deliver the exact 3D needle location. Thus, also the part inserted inside the patient is provided. A dotted line 420 indicates the portion arranged inside the body, whereas a straight line 422 indicates the portion of the needle arranged outside the body.

In a second embodiment, the a-priori knowledge of the needle length is combined with the 3D position of the needle fragment from the optical cameras, such that the exact location within the patient's anatomy is known for stiff, straight needles.

In a third embodiment, both described approaches (using the X-ray image and using a-priori knowledge of the needle length) can be combined to verify the respective results, and indicate the uncertainty of the position.

Figure 9D:
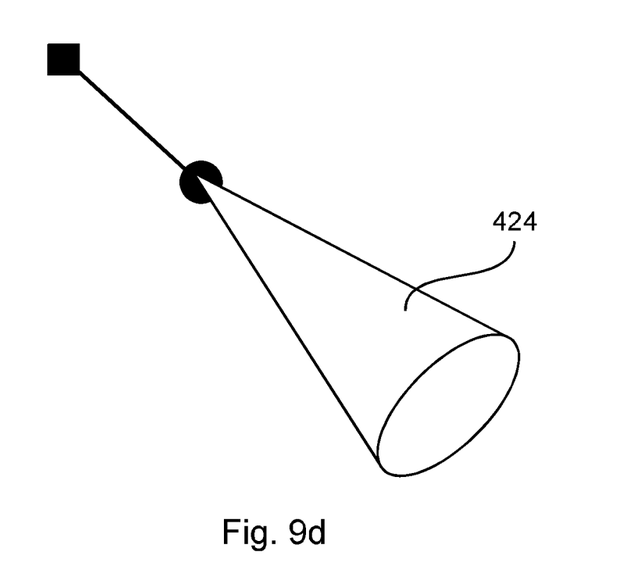

In a further exemplary embodiment, relating to bending needles, shown in FIG. 9d, it can also be very useful to track the visible needle fragment from the optical cameras. Using the a-priori known needle length, a volumetric region 424 can be indicated, regarding the expected position of the needle. It can be taken into account that increasing bending angles are increasingly unlikely. The confidence region can then be visualized in the fused images.

Figure 9E:
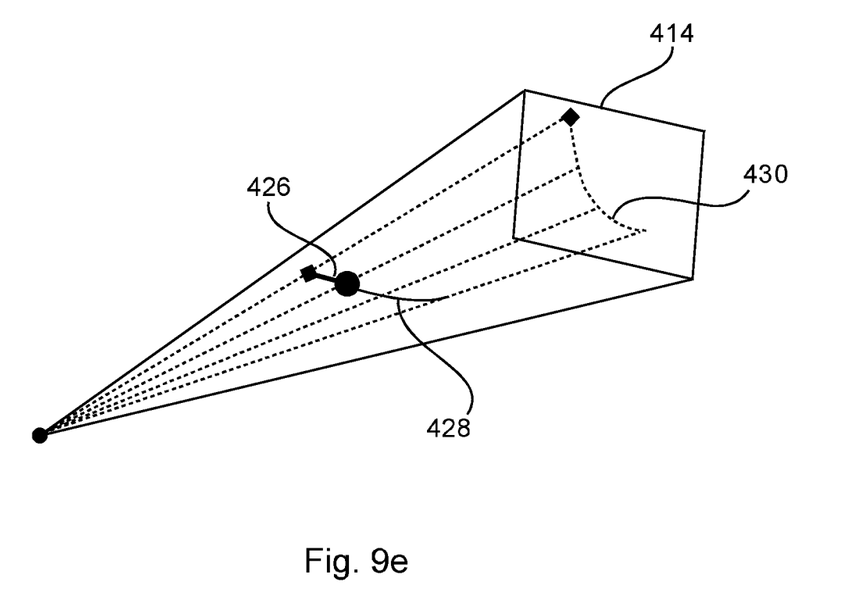

In a further exemplary embodiment, this method can be further defined by estimating the bending in the hidden needle fragment by extrapolating any bending found in the optically visible needle fragment. For example, FIG. 9e relates to a further exemplary embodiment, where the tracked needle fragment in 3D from the optical cameras is combined with the a-priori knowledge of the needle length, the X-ray image, and a simple model for the bending of the needle, it is possible to find or several possible solutions that fit all information. FIG. 9e indicates the portion of the needle arranged outside the body, indicated with straight line 426, as described above, and in combination a predicted needle, indicated with thinner straight line 428. On the X-ray detector 414, the respective projection 430 is shown. For example, as a bending model, a second degree polynomial or spline is used, together with the 3D optically visible fragment 426 and the X-ray image, i.e. the projection 430, can be used to predict the actual 3D bended needle part 428.

Figure 11:
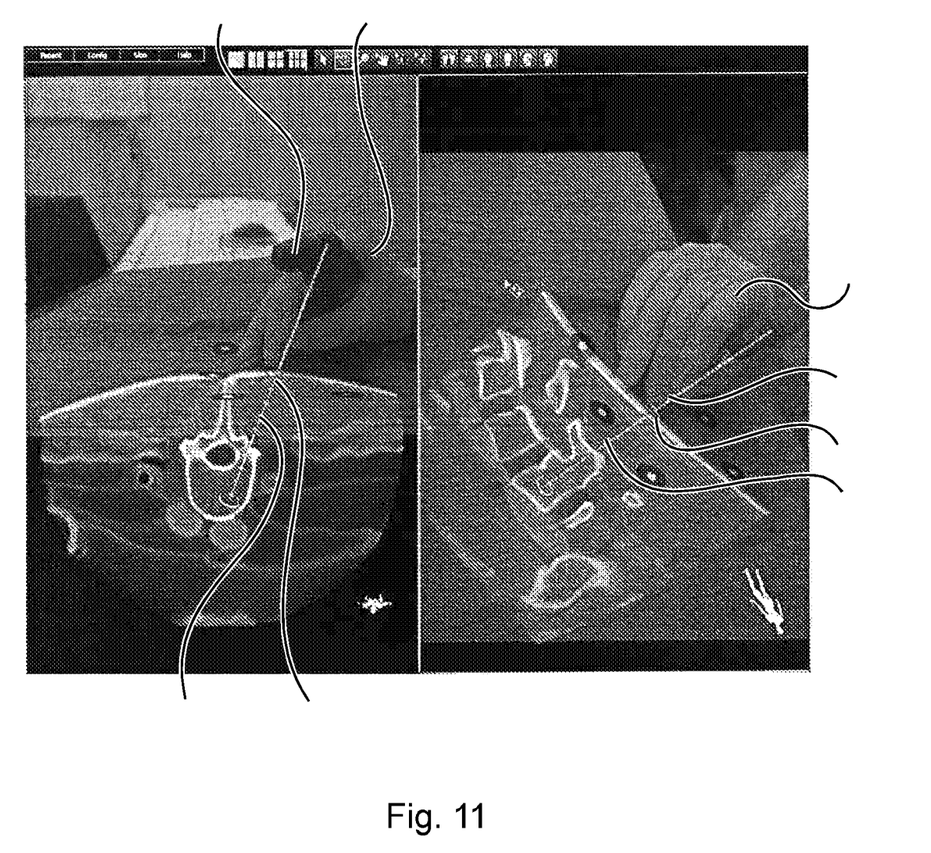
FIG. 11 shows a greyscale illustration of FIG. 7.
Figure 12:
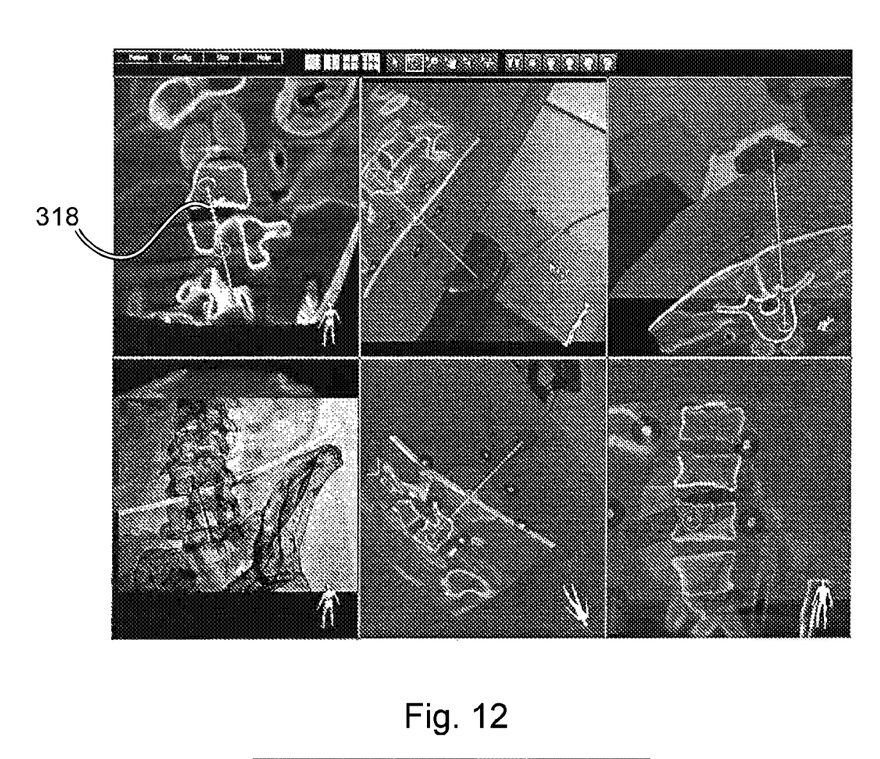
FIG. 12 shows an illustration of FIG. 8.
Figure 13:
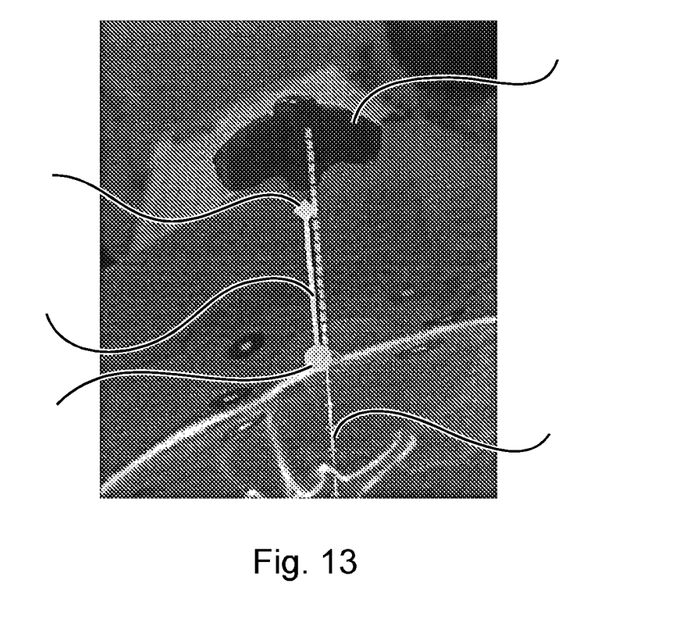
FIG. 13 shows a graphical representation of FIG. 10.

FIG. 11 shows a graphical representation of the line drawing of FIG. 7, FIG. 12 shows a graphical representation of FIG. 8 and FIG. 13 shows a graphical representation of FIG. 10.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging system for tracking an interventional device, comprising:
   an interface; and
   at least one processor;
   wherein the interface is configured to:
   provide a first 2D image and a second 2D image of a first part of an interventional device, which first part is arranged outside an object;
   project the first 2D image and the second 2D image in 3D space;
   determine an intersection of the projected first 2D image and the projected second 2D image with each other in the 3D space;
   wherein the interface is configured to provide second image data of a second part of the interventional device, which second part is a spatial continuation of the first part, and which second part is arranged at least partially inside the object;

wherein the second image data comprises 2D image data;

wherein the at least one processor is configured to
compute a first 3D model portion of the interventional device including modelling of bending of the first part of the interventional device based on the determined intersection of the first and second 2D images of the first part of the interventional device by modelling bending of the interventional device for the first 2D image and the second 2D image using a bending model for the bending of the interventional device; and to compute a second 3D model portion of the interventional device based on combining the 2D image data of the second part of the interventional device with the determined intersection of the first 3D model portion by predicting bending of the interventional device inside the object by extrapolating the determined bending in the first 2D image and the second 2D image; and wherein the interface is configured to provide data of a graphical representation of the interventional device based on forming a model by combining the first and second 3D model portions, the graphical representation being indicative of a facilitated, real time tracking of the interventional device moving through the object based on the first 3D model, the first 2D image and the second 2D image, and the second image data.

2. The system according to claim 1, comprising a display configured to display a graphical representation of the interventional device based on the first and second 3D model portions.

3. The system according to claim 2, wherein the at least one processor is configured to register the projected first 2D image and the projected second 2D image and the second 2D image data; and wherein the display is configured to display the projected first 2D image and the projected second 2D image and the second 2D image data in a combined image together with a model representation of the interventional device based on the first and second model portions.

4. The system according to claim 1, further comprising:
a first image acquisition device; and
a second image acquisition device;
wherein the first image acquisition device is configured to acquire the first 2D image and the second 2D image;
wherein the second image acquisition device is configured to acquire the second image data.

5. The system according to claim 1, wherein the first 2D image and the second 2D image is provided by at least two optical cameras; and
wherein the second image data is provided by at least one of:
i) an X-ray imaging arrangement; and
ii) ii) an ultrasound imaging arrangement.

6. The system according to claim 1, wherein the at least one processor is configured to combine the first model portion and the second model portion to form a 3D model of the interventional device.

7. The system according to claim 1, wherein the at least one processor is configured to determine a bounding space, in which the interventional device is located; and wherein the at least one processor is configured to determine the bounding space based on the first model portion and the second model portion; and/or on the model of the interventional device.

8. The system according to claim 1, wherein the at least one processor is configured to determine a bounding box, in which a predetermined part of the interventional device is located.

9. The system according to claim 1, wherein the interventional device is a flexible interventional device configured for a bending in simple curve geometries;
and wherein the at least one processor is configured to determine two possible bending poses of the interventional device; and wherein a display is configured to present the bending poses to the user.

10. The system according to claim 1, wherein the at least one processor is configured to register the projected first 2D image and the projected second 2D image and the second 2D image data; and
wherein a display is configured to display the registered images in a combined image.

11. A method for tracking an interventional device inserted partially inside an object, comprising the following steps:
a) with a first image acquisition device, acquiring first image data of a first part of an interventional device, which first part is arranged outside an object, wherein the first image data comprises at least two 3D images;
b) with a second image acquisition device, acquiring second image data of a second part of the interventional device, which second part is a spatial continuation of the first part, and which second part is arranged inside the object; wherein the second image data comprises 2D image data;
c) with at least one processor, determine an intersection of the at least two 3D images of the first image data with each other in a 3D space;
d) with the at least one processor, computing a first 3D model portion of the interventional device based on the determined intersection of the first image data by operations including:
modelling bending of the interventional device for the first image data using a bending model for the bending of the interventional device;
e) with the at least one processor, computing a second 3D model portion of the interventional device based on the second image data and the determined intersection in the first model portion by predicting bending of the interventional device inside the object by extrapolating the determined bending in the first image data; and
f) with a user interface, performing real time tracking of the interventional device moving through the object based on the first 3D model, the first image data, and the second image data, the real time tracking including displaying a graphical representation of the interventional device based on the first and second 3D model portions.

12. The method according to claim 11, wherein the computing of the second model portion is also based on a predetermined length of the interventional device.

13. A non-transitory computer readable medium storing a computer program being executed by a processing unit that is adapted to control a medical imaging system to perform the method of claim 11.

14. A medical imaging system for tracking an interventional device, comprising:

a first imaging device comprising at least two optical cameras configured to generate first image data of a first part of an interventional device, the first part being arranged outside an object and comprising 3D image data;

a second imaging device configured to generate second image data of a second part of the interventional device, the second part being a spatial continuation of the first part, the second part is arranged at least partially inside the object, the second image data comprising 2D image data;

at least one processor programmed to:

compute an intersection of at least two 3D images in the 3D image data;

compute a first 3D model portion of the interventional device based on the computed intersection of the first image data by modelling bending of the interventional device for the first image data using a bending model for the bending of the interventional device;

compute a second 3D model portion of the interventional device based on the second image data and the computed intersection in the first model portion by predicting bending of the interventional device inside the object by extrapolating the determined bending in the first image data; and an interface configured to provide data of a graphical representation of the interventional device based on the first and second 3D model portions, the interface performing real time tracking of the interventional device moving through the object based on the first 3D model, the first image data, and the second image data, the real time tracking including displaying the graphical representation of the interventional device.

15. The system according to claim 14, wherein the second imaging device includes at least one of:
   an X-ray imaging arrangement; or
   an ultrasound imaging arrangement.

16. The system according to claim 14, wherein the at least one processor is further reprogrammed to register the first 3D image data and the second 2D image data; and
   further including a display configured to display the first 3D image data and the second 2D image data in a combined image together with a model representation of the interventional device based on the first and second model portions.

17. The system according to claim 16, wherein the at least one processor is further programmed:
   to determine a bounding space, in which the interventional device is located, based on at least one of the first model portion, the second model portion, and the graphical representation of the interventional device.

18. The system according to claim 17, wherein the at least one processor is configured to determine a bounding box, in which a predetermined part of the interventional device is located.

19. The system according to claim 14, wherein the bending model comprises a second degree polynomial bending model or a spline bending model.

* * * * *